United States Patent [19]

Weisgerber et al.

[11] 4,446,327
[45] May 1, 1984

[54] PROCESS FOR THE PREPARATION OF 3-CHLOROPHTHALIDE

[75] Inventors: Greger Weisgerber, Königswinter; Klaus-Dieter Steffen, Hennef, both of Fed. Rep. of Germany

[73] Assignee: Dynamit Nobel Aktiengesellschaft, Troisdorf, Fed. Rep. of Germany

[21] Appl. No.: 375,637

[22] Filed: May 6, 1982

Related U.S. Application Data

[63] Continuation of Ser. No. 154,736, May 30, 1980, abandoned, which is a continuation of Ser. No. 13,498, Feb. 21, 1979, abandoned, which is a continuation of Ser. No. 782,486, Mar. 29, 1977, abandoned.

[30] Foreign Application Priority Data

Apr. 3, 1976 [DE] Fed. Rep. of Germany ....... 2614449

[51] Int. Cl.$^3$ ............................................ C07D 307/77
[52] U.S. Cl. .................................................. 549/307
[58] Field of Search ......................................... 549/307

[56] References Cited

U.S. PATENT DOCUMENTS 2,748,161  5/1956  Head et al. ................... 549/307 X
3,663,575  5/1972  Roos et al. ........................ 549/307
3,787,447  1/1974  Raoul ................................ 549/307

FOREIGN PATENT DOCUMENTS 520230      1/1956   Canada ............................. 549/307
1154809     9/1963   Fed. Rep. of Germany ...... 549/307
2137553     2/1973   Fed. Rep. of Germany ...... 549/307
46-7229338 10/1971   Japan .
1233086     5/1971   United Kingdom ............... 549/307

OTHER PUBLICATIONS

Ralyohn, Journ. Amer. Chem. Soc., vol. 76, pp. 5479–5481 (1954).

Primary Examiner—Nicky Chan
Attorney, Agent, or Firm—Felfe & Lynch

[57] ABSTRACT

A process is provided for the direct hydrolysis of pentachloro-o-xylene to 3-chlorophthalide in high yield and high purity by carrying out the hydrolysis with 2 mols of water in the presence of a catalyst at a temperature above 100° C., proportioning the water uniformly during the reaction time so that it immediately reacts completely and does not leave the reaction vessel in vapor form.

7 Claims, No Drawings

PROCESS FOR THE PREPARATION OF 3-CHLOROPHTHALIDE

This is a continuation application of Ser. No. 154,736 filed May 30, 1980, now abandoned; which is a continuation of Ser. No. 013,498 filed Feb. 21, 1979, now abandoned which is a continuation of Ser. No. 782,486, filed Mar. 29, 1977, now abandoned.

BACKGROUND

The invention concerns a process for the preparation of 3-chlorophthalide by the hydrolysis of o-pentachloroxylene with water.

3-Chlorophthalide, which is also known as 3-chloro[3H]-isobenzofuranone-1, or as the pseudochloride of phthalaldehydic acid, and is abbreviated hereinbelow as 3-CP, serves in addition to 3-bromophthalide as an intermediate for the introduction of the phthalidyl moiety in organic syntheses.

3-Chlorophthalide is prepared by classical methods either by the chlorination of phthalide or from phthalaldehydic acid and thionyl chloride (Gabriel, Berichte 49, [1916] 1612):

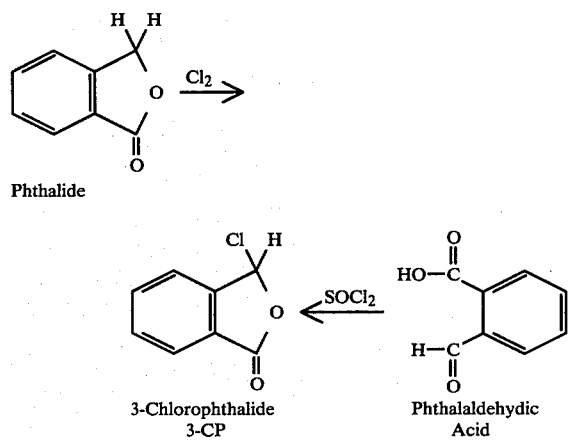

Both processes, however, set out from compounds which themselves must be prepared by a multiple-step synthesis.

3-Chlorophthalide, however, can also by prepared by hydrolysis of pentachloro-o-xylene (α,α,α,α',α'-pentachloro-o-xylene or o-dichloromethyltrichloromethylbenzene), abbreviated hereinbelow as o-PCX, which is easily obtainable by the chlorination of o-xylene.

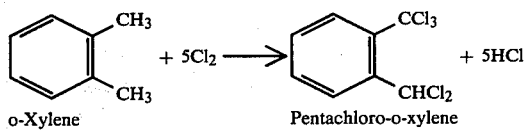

It is known, however, that this hydrolysis of o-PCX is difficult and does not easily result in 3-CP. For, if o-PCX is hydrolyzed conventionally with an excess of water, phthalaldehydic acid (PAA) will be obtained; see, for example, U.S. Pat. No. 2,748,161.

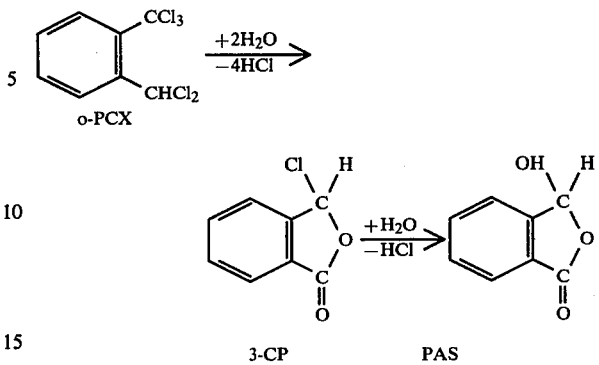

If one uses not an excess but the stoichiometric amount of water, of 3 moles, the reaction has to be catalyzed, since otherwise no reaction will take place. In these cases, too, the hydrolysis cannot be stopped at the 3-chlorophalide stage, but runs to the final phthaladehydic acid stage (as described, for example, in German Democratic Republic Pat. No. 9443).

This shows that all methods described in the literature for the direct hydrolysis of pentachloro-o-xylene fail to lead to 3-chlorophthalide.

Now, another possibility consisted in hydrolyzing with water in bound form instead of free water, using mono- or dicarboxylic acids which, under the conditions of the reaction, are themselves transformed to the carboxylic acid anhydrides or carboxylic acid chlorides, respectively, with the yielding of water.

Thus Rabjohn, for example, in J. Amer. Chem. Soc. 76 (1954), pp. 5479–81, describes the preparation of 3-chlorophthalide from o-PCK- and maleic acid in the presence of zinc chloride.

In a Japanese patent application (Published Patent Application 29338/72 JA 10.3.71-12959/71), 3-CP is obtained in addition to another acid chloride by the reaction of 2 moles of an aromatic monocarboxylic acid with 1 mole of o-PCX in the presence of iron(III) chloride:

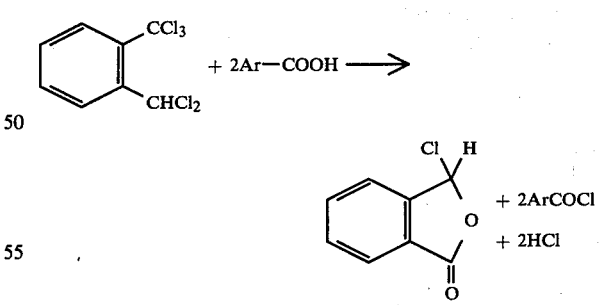

It is possible by these methods to hydrolyze pentachloro-o-xylene to 3-chlorophthalide, but then by-products—substantially acid chlorides—are produced in such great amounts that a difficult separation by a complicated distillation process becomes necessary, and the yield and purity of the desired product are affected. In addition, the economy of these processes is questionable unless the economical utilization of the by-products, especially acid chloride, which are produced in as much as twice the amount, is not assured.

THE INVENTION

It is an object of the present invention to provide a process permitting 3-chlorophthalide to be produced by the hydrolysis of pentachloro-o-xylene. Another object was to find a process which will enable the hydrolysis to be carried out only to the chlorophthalide stage, and can be performed with a hydrolyzing substance which itself yields a volatile reaction product, such as water, which in the hydrolysis is transformed to hydrochloric acid. It is furthermore an object of the present invention to find a process permitting the preparation of 3-chlorophthalide in high purity and with a great yield.

Surprisingly, it has been found that a direct hydrolysis of pentachloro-o-xylene to 3-CP with a high yield and high purity is possible if the hydrolysis is performed with 2 moles of water in the presence of certain catalysts at temperatures above 100° C., proportioning the water uniformly during the reaction time such that it immediately reacts completely and does not leave the reaction vessel in vapor form. This finding is all the more surprising since the reaction will not take place at all at the above-named temperatures in the absence of a catalyst. It was not obvious that the use of the stoichiometric amount of water under the described reaction conditions would lead to success, since after the first proportioned addition of water a mixture of pentachloroxylene and chlorophthalide is present and it was to be expected that, upon the further addition of water, both the pentachloroxylene and the chlorophthalide would be saponified, so that the end effect to be expected according to the above-named literature was complex mixtures containing phthalaldehydic acid.

Suitable catalysts are acids, such as sulfuric acid, phosphoric acid and compounds commonly referred to as Friedel-Crafts catalysts or Lewis acids, such as for example antimony(V) chloride, bismuth(III) chloride, zinc chloride, cadmium chloride, thallium(III) chloride, and metal chlorides of Groups IV to VIII of the periodic table of the elements, such as those of vanadium, molybdenum, tungsten, manganese or iron. Those compounds can also be used instead of the chlorides, which under the conditions of the reaction are transformed to the chlorides, such as for example oxides, carbonates, salts of organic acids, alcoholates, and in some cases even the metal itself. Examples of especially suitable compounds of the group of the transitional metal compounds are: vanadium(V) oxide, vanadyl(V) tri-n-butylate, molybdenum(VI) oxide, molybdenum(V) chloride, tungsten(VI) oxide, tungsten(VI) chloride, iron, iron(II) oxide, iron(III) oxide, iron(II) chloride, and iron(III) chloride.

Of these catalysts those are especially suitable which dissolve in the reaction mixture and are not irreversibly degraded by water in the presence of HCl.
*Water soluble catalysts, such as for example $FeCl_3$ or $ZnCl_2$, also may be used in form of a solution in water.

The catalysts can be used individually or in mixture in amounts of about 0.01 to about 5 g per mol of pentachloroxylen preferably in amounts of about 0.05 to about 0.5 g. The reaction temperature amounts to about 100° to about 180° C., preferably about 120° to about 150° C., at standard pressure.

The process described by the invention operates preferably at standard pressure. Higher and lower pressures are basically possible, but very complex on account of the technically difficult removal of the gaseous hydrogen chloride which forms in great amounts in the reaction.

Although the water is normally proportioned to the reaction mixture which has been raised to temperature, i.e., it is introduced into the into the melted pentachloroxylene, it can also be proportioned as steam, if a precise proportioning apparatus makes it possible to adhere to the amounts of water called for.

The amount of water used is between 1.8 and 2.2 moles per mole of pure pentachloroxylene; it is preferably precisely 2 moles. For it has been found that, even when the water excess is slight, the yield decreases considerably, whereas a slight insufficiency yields a complex mixture of starting products and by-products, i.e., it greatly impairs the quality of the chlorophthalide formed.

Another characteristic of the process described by the invention consists of the fact that the water is added, not all at once, but step by step.

The proportioning of water in liquid or gaseous state is preferably performed continuously, but it can also be done intermittently, e.g., by means of a timing circuit. The proportioning rate is to be selected in such a manner that the water reacts completely and does not leave the reactor as steam. Accordingly, it will depend on the reaction temperature, the activeness of the catalyst, and the distribution of the water or vapor, as the case may be, in the organic phase, i.e., on the stirring speed, the shape of the stirrer, the fittings inside the reactor, etc. The rate of addition of the water amounts, for example, to from about 10 to about 100 g of $H_2O$ per hour and liter of reactor volume, but it can easily be above or below these amounts.

3-CP is an intermediate usable for many purposes e.g. by forming o-phthalic aldehyde acide by hydrolysis or by forming phthalidyl derivates as e.g. O-ethyl-S-(3-phthalidyl)xanthate according to J. org. Chem. 37, (1972) 1375 which compounds are usable fugicides as known by Japanese application 73 11012.

EXAMPLES

EXAMPLES 1-7

The reaction vessel is a 500-milliliter four-necked flask heated with an oil bath and equipped with stirrer, reflux condenser, contact thermometer and introduction tube. From the reflux condenser a PVC hose runs to a cooled water receiver equipped for cooling and stirring, in which the hydrogen chloride gas is absorbed. The injection of the water is performed with a 50-ml injection syringe provided with a controllable, motor-powered plunger drive.

In this reactor, 284 g of 98% pentachloroxylene (1 mole) is placed, together with the catalyst, at the temperature given in Table 1, and is vigorously stirred. After 5-10 minutes, the water injection is started and 36 g (2 moles) of water is injected, with constant stirring, over a period of one to 1½ hours, at a uniform rate. The formation of HCl begins at once; the transformation can be determined on the basis of the amount of hydrochloric acid absorbed. When all the water has been injected, stirring is continued for another one-half hour to one hour. In Examples 2 to 7 a complexing agent is added, and the raw 3-chlorophthalide is distilled at a vacuum of 2 to 5 Torr. The boiling point is 116° to 118° C./3 Torr. The yield of 3-chlorophthalide and the purity of the product are shown in Table 1.

EXAMPLE 8

The reaction vessel is a heated four-liter four-necked flask with stirrer, reflux condenser, contact thermometer and introduction tube. From the top of the reflux condenser a PVC hose runs to an HCl absorption vessel, and the introduction tube is connected to a water proportioning pump. 3292 g of 96 wt-% pentachloroxylene (=11.3 moles) is placed at 140° C. in the reaction vessel with 2 g of FeCl$_3$. Ten minutes later, with vigorous agitation, the reaction is started up by turning on the water pump, and sustained at 140° C. by feeding 120 ml of water per hour into the reactor. When 409 g (22.7 moles) of H$_2$O has been added, the reaction is allowed to continue for another hour without supplying any more water. 1690 g of HCl=102% of the theory is absorbed. The raw 3-chlorophthalide is distilled in vacuo through a small packed column; B.P. 110°–112° C. at 2 Torr. 1800 g (95% of the theory) is obtained of 3-CP with a purity (determined by gas chromatography) of 97.5%. The melting point is 58° to 60° C.

EXAMPLE 9

560 kg of 98% molten o-PCX (=2000 moles) is placed in an enameled 500-liter stirring kettle equipped with a double jacket, a stirrer drive, a reflux condenser and an inlet connection. As soon as the temperature of 140° C. is reached, 300 g of FeCl$_3$ is injected with the aid of an additional 10 kg of pentachloroxylene. Then 72 kg (4000 moles) of water is injected from the bottom with a piston-type proportioning pump, at a rate of 10 l/h. The HCl gas emerging from the top of the reflux condenser is monitored with a flow meter (approx. 25 cu.m./h) and absorbed with water in a packed column in the form of 35% hydrochloric acid. After completion of the water injection, the reaction is allowed to continue for another 2 hours, and then the raw product, which consists of 91% of 3-chlorophthalide and 9% of distillation residue, as determined by distillation of a specimen, is delivered to the vacuum still. The distillation is performed with a column (diameter 20 cm, length 150 cm) packed with Raschig rings, with a reflux ratio of 1:2, at a vacuum of 4 Torr; the boiling point is 124° C. 302 kg of distillate is obtained, equal to 90% of the theoretical yield, with a purity of 99.2–99.5% (determined by gas chromatography). The distillation residue amounts to about 40 kg.

EXAMPLES 10-12 GIVEN FOR COMPARISON

Examples 10 and 11 show that, without the addition of catalyst, even under pressure, no reaction takes place between pentachloroxylene and water to yield 3-CP. Example 12 shows that, if only one mole of water is used per mole of o-PCX, mostly unreacted o-PCX will result, in addition to 3-CP.

EXAMPLE 10 (FOR PURPOSES OF COMPARISON)

In a two-liter four-necked flask equipped with a stirrer, reflux condenser, thermometer and a dropping funnel with a long tube, 1114 g of pure o-PCX (4 moles) was maintained at 140° C. Then an attempt was made to fed water into it drop by drop below the surface of the molten o-PCX. Over a period of 15 hours, only 10 ml of H$_2$O was fed in. If the feeding was more rapid, the temperature immediately dropped to about 110° C. In no case was any formation of HCl gas found to take place.

EXAMPLE 11 (FOR PURPOSES OF COMPARISON)

In a one-liter glass autoclave with stirrer and temperature indicator, 1114 g of pure o-PCX (4 moles) was heated with 144 ml of H$_2$O (8 moles) for 6 hours at 135° C., at the pressure produced by the reactants. Then the reaction had to be stopped on account of the excessive internal pressure. After the stirrer was shut off, the aqueous top phase was still present in virtually the same depth, and from it 30 g of a crystallizate precipitated upon cooling; it had a melting point of 97°–99° C. and was identified as phthalaldehydic acid. From this amount of PAA, an o-PCX transformation of 5% was calculated. No 3-CP was found.

TABLE 1

| | | Examples 1–7 | | | | |
|---|---|---|---|---|---|---|
| Example | Catalyst | Amount | Temperature °C. | Yield in g (% of theory) | | Purity %[1] | Distillation residue in grams |
| 1 | H$_2$SO$_4$[2] | 2 ml | 130 | 126 | (75) | 94.9 | 40 |
| 2 | Fe powder | 0.1 g | 120 | 153 | (91) | 98.9 | 14[4] |
| 3 | BiCl$_3$ | 2 g | 130 | 140 | (83) | 96.6 | 25 |
| 4 | ZnCl$_2$ | 2 g | 130 | 135 | (80) | 98.6 | 30 |
| 5 | TlCl$_3$ | 2 g | 130 | 157 | (93) | 98.9 | 10 |
| 6 | VO(OBu)$_3$[3] | 2 ml | 150 | 145 | (86) | 96 | 20 |
| 7 | MoO$_3$ | 0.2 g | 140 | 162 | (96) | 98.8 | 5[4] |

[1]As determined by gas chromatography, FID area %
[2]Conc., approx. 95%
[3]Vanadyl (V) tri-n-butylate
[4]Addition of 0.4 g of ethylenediamine tetracetic acid prior to distillation.

EXAMPLE 12 (FOR PURPOSES OF COMPARISON)

In a one-liter four-necked flask, with equipment similar to Examples 1–3, 568 g of 98% o-PCX (2 moles) was reacted by the procedure described therein, with 36 g (2 moles) of H$_2$O over a period of 2 hours at 130°–140° C., with the addition of 0.4 g of FeCl$_3$. After the vacuum distillation (B.P. 145°–149° C., 11 Torr), 403 g of distillate is obtained, and 42 g of residue. According to gas chromatographic analysis, 41% of the distillate consists of 3-CP and 53% of o-PCX. Approximately 1% of o-dichloromethylbenzoyl chloride is present in the mixture, the balance was not tested.

What is claimed is:
1. Process for the preparation of 3-chlorophthalide by hydrolysis of pentachloro-o-xylene, characterized in that pentachloro-o-xylene is hydrolyzed with 1.8–2.2 mols of water per mol of pentachloro-o-xylene at temperatures above 100° C., in the presence of a Lewis acid catalyst, by proportioning of the water into the reaction mixture at the rate at which it reacts to form HCl.
2. Process of claim 1, characterized in that the amount of water used is 1.98–2.02 mols per mole of pentachloro-o-xylene.

3. Process of claim 1, characterized in that the catalysts dissolve in the reaction medium and are not irreversibly degraded by water in the presence of HCl.

4. Process of claim 3, characterized in that the catalysts are used singly or in mixture with amounts of about 0.01 to about 5 g per mole of pentachloro-o-xylene.

5. Process of claim 4, characterized in that the catalysts are used singly or in mixture with amounts of about 0.05 to about 0.5 g per mole of pentachloro-o-xylene.

6. Process of claim 1, characterized in that the hydrolysis is performed at temperatures between about 100° and about 180° C.

7. Process of claim 1, characterized in that the hydrolysis is performed at temperatures between about 120° to about 150° C.

* * * * *